United States Patent
Yagi et al.

(10) Patent No.: US 8,005,279 B2
(45) Date of Patent: Aug. 23, 2011

(54) CAPSULE ENDOSCOPE IMAGE DISPLAY CONTROLLER

(75) Inventors: Yasushi Yagi, Hyogo (JP); Tomio Echigo, Osaka (JP); Ryusuke Sagawa, Osaka (JP); Hai Vu, Osaka (JP)

(73) Assignee: Osaka University, Osaka (JP)

( * ) Notice: Subject to any disclaimer, the term of this patent is extended or adjusted under 35 U.S.C. 154(b) by 1055 days.

(21) Appl. No.: 11/883,551

(22) PCT Filed: Dec. 19, 2005

(86) PCT No.: PCT/JP2005/023272
§ 371 (c)(1),
(2), (4) Date: Aug. 2, 2007

(87) PCT Pub. No.: WO2006/100808
PCT Pub. Date: Sep. 28, 2006

(65) Prior Publication Data
US 2008/0119691 A1    May 22, 2008

(30) Foreign Application Priority Data
Mar. 22, 2005    (JP) .................................. 2005-082735

(51) Int. Cl.
*G06K 9/00* (2006.01)
(52) U.S. Cl. ....................................... 382/128; 600/109
(58) Field of Classification Search .................. 382/128; 600/424, 109
See application file for complete search history.

(56) References Cited

U.S. PATENT DOCUMENTS
7,011,625 B1 *    3/2006    Shar .............................. 600/109
(Continued)

FOREIGN PATENT DOCUMENTS
EP    1 681 009    7/2006
(Continued)

OTHER PUBLICATIONS

1: "M2A (R) Capsule Endoscopy Given (R) Diagnostic System", [online], Given Imaging Ltd., [searched on Mar. 9, 2005], Internet <URL: http//www.givenimaging.com/NR/rdonlyres/76C20644-4B5B-4964-811A-071E8133F83A/0/GI_Marketing_Brochure_2003.pdf> (Given® Diagnostic System; The Platform for PillCam™ Endoscopy).

(Continued)

*Primary Examiner* — Hadi Akhavannik
(74) *Attorney, Agent, or Firm* — Wenderoth, Lind & Ponack, L.L.P.

(57) ABSTRACT

The present invention discloses a capsule endoscope image display controller (26) including: an image-to-image similarity calculating unit (36) that calculates, for each image included in an image sequence captured by a capsule endoscope which moves within the digestive organs, a similarity between the image and its temporally consecutive image; an amount-of-movement calculating unit (47) that calculates, for each image included in the image sequence, an amount of movement of a feature area included in the image; a video state classifying unit (41) that classifies, for each image included in the image sequence, a video state of the image into one of the following states, based on the video state, the similarity, and the amount of movement of the image: (a) "stationary state" indicating that the capsule endoscope is stationary, (b) "digestive organs deformation state" indicating that the digestive organs are deformed, and (c) "capsule moving state" indicating that the capsule endoscope is moving, based on the similarity and the amount of movement of the image; a rendering duration determining unit (42) that determines, for each image included in the image sequence, a rendering duration between the image and its temporally consecutive image; and a display controlling unit (44) that sequentially displays, on a screen, the images included in the image sequence with the determined rendering durations.

12 Claims, 7 Drawing Sheets

U.S. PATENT DOCUMENTS

| | | | |
|---|---|---|---|
| 7,801,584 B2 * | 9/2010 | Iddan et al. | 600/407 |
| 2003/0040685 A1 * | 2/2003 | Lewkowicz et al. | 600/593 |
| 2004/0111011 A1 | 6/2004 | Uchiyama et al. | |
| 2004/0176684 A1 * | 9/2004 | Tabuchi et al. | 600/424 |
| 2004/0249291 A1 * | 12/2004 | Honda et al. | 600/476 |
| 2004/0258328 A1 * | 12/2004 | Adler | 382/286 |
| 2004/0264754 A1 * | 12/2004 | Kleen et al. | 382/128 |
| 2005/0143623 A1 * | 6/2005 | Kojima | 600/109 |
| 2006/0189843 A1 | 8/2006 | Nakamura et al. | |

FOREIGN PATENT DOCUMENTS

| | | |
|---|---|---|
| JP | 10-243351 | 9/1998 |
| JP | 2004-41709 | 2/2004 |
| JP | 2004-321603 | 11/2004 |
| JP | 2005-124965 | 5/2005 |
| WO | 2004/096027 | 11/2004 |

OTHER PUBLICATIONS

B. Shahraray, "*Scene change detection and content-based sampling of video sequences,*" Proc. IS&T/SPIE 2419, pp. 2-13, 1995.

D. Swanberg, C.F. Shu, R. Jain, "*Knowledge Guided Parsing in Video Databases,*" Proc. SPIE Conf., vol. 1908, 1993, pp. 13-24.

\* cited by examiner

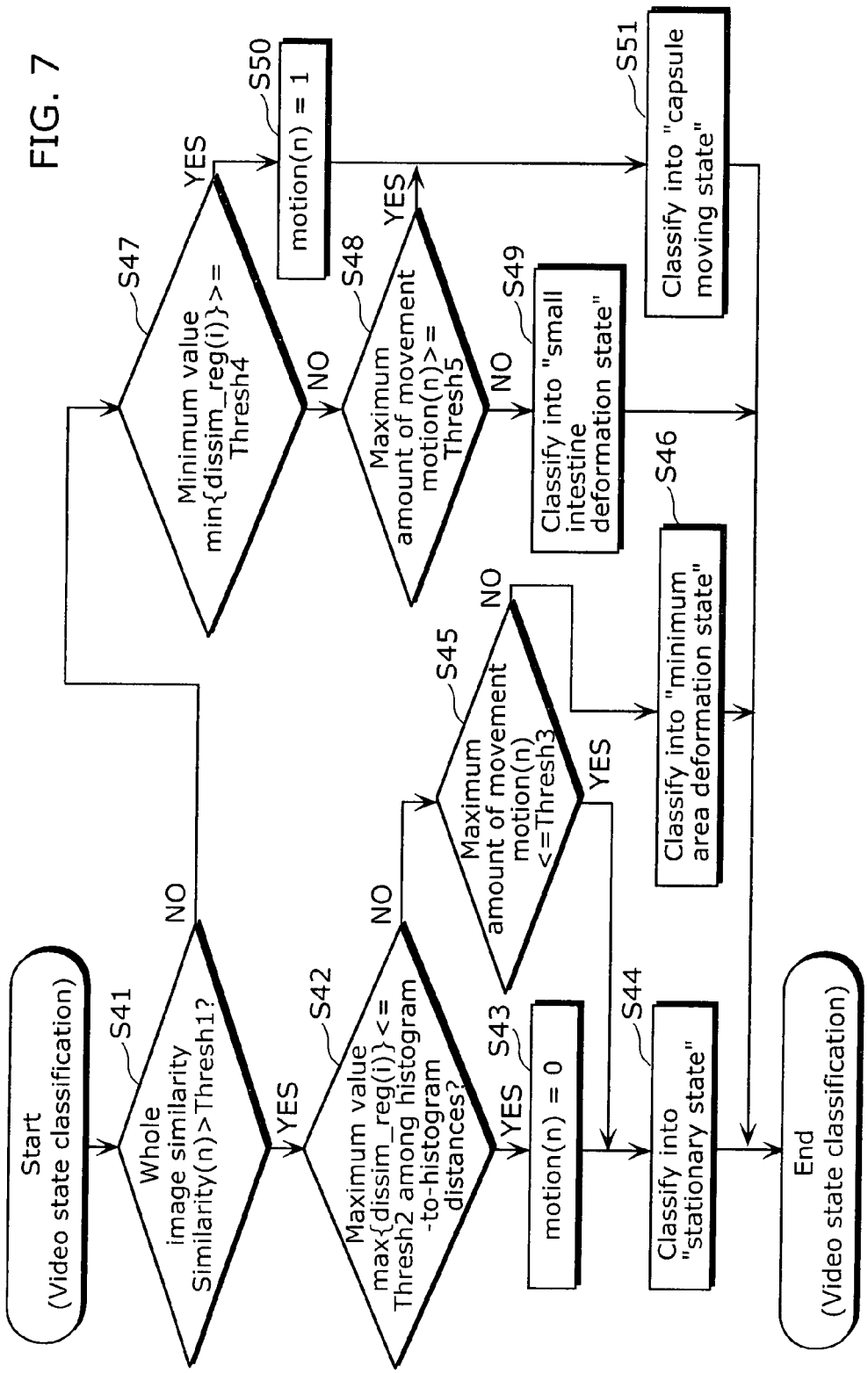

CAPSULE ENDOSCOPE IMAGE DISPLAY CONTROLLER

TECHNICAL FIELD

The present invention relates to an image display controller, and more particularly to a capsule endoscope image display controller that performs display control of an image sequence captured by a capsule endoscope.

BACKGROUND ART

In recent years, in the medical field, a capsule endoscope (see, for example, Non-Patent Document 1) has begun to be used to carry out an image examination of the digestive organs. It is considered at present that a capsule endoscope is effective for an examination of the small intestine which has been difficult to capture in video using a conventional probe-type endoscope.

However, it takes about eight hours for a capsule endoscope to be passed through the small intestine which is approximately five to six meters long when extended. Accordingly, the entire eight-hour video obtained by the capsule endoscope becomes a target of examination, placing the burden on a doctor who carries out the examination. Hence, at present, the examining doctor performs manual operations for high- and low-speed playback while observing a video and staring at the video so as not to overlook a sudden, unpredictable change, that is, the appearance of the lesion. In view of this, there is a demand for short-time video display that reduces a burden on the examining doctor and enables him/her to maintain concentration to avoid oversight.

While in the current probe-type endoscope, the digestive organs are observed by inserting a probe, the capsule endoscope allows a capsule that is swallowed by a test subject to be propelled by peristaltic movement of the digestive organs, as with the passing of food, and a video is continuously shot as long as a battery lasts. The movement of the capsule is advanced according to the physical condition of the test subject, as with the movement of food, and thus such examination is not burdensome for the test subject. However, since image capturing takes a long time, the examining doctor needs to examine such video for a long time. However, in practice, since the movement of a capsule is slow, it is often the case that very similar images continue for a long time.

In display of such an image sequence, even if frames are advanced at a speed higher than a normal speed, it does not cause any problem in examination, and thus at present, the examining doctor performs fast-forwarding by an interactive operation. In the current operation, the doctor performs, by his/her decision, fast-forwarding with respect to a frame rate which is a constant speed, and thus, fast-forwarding is limited so as to prevent the doctor from overlooking the legion when a sudden movement of a capsule or a sudden movement of the small intestine occurs. In addition, when fast-forwarding speed exceeds the limitations, there is the complexity of having to rewind the video, reduce the speed, and restart the examination. In addition, in order not to overlook a big change in a partial area at the time of fast-forwarding, the doctor is required to concentrate heavily, which is a significant burden on him/her. Thus, it takes about three hours for a beginner of an examination to carry out an examination of an eight-hour video and it takes about one hour even for a skilled person to carry out such an examination. Accordingly, there is a demand for a support technique for realizing an examination that takes only a short time.

Meanwhile, in video processing, it is possible to automatically detect its state. Such a technique is used as a technique for detecting a cut point in a video. In conventional cut point detection, a shot cut is detected by determining how many blocks have similarity in the whole image, based on a square sum of differences between luminance values of small blocks in adjacent images (see, for example, Non-Patent Document 2) and a similarity between histograms of blocks (see, for example, Non-Patent Document 3), or the like. However, this technique is intended to determine whether there is a cut and is not intended to convert a similarity between consecutive adjacent images into numbers and change the display speed. A method has also been proposed for changing the frame-to-frame rate based on MPEG (Moving Picture Experts Group) motion compensation information (see, for example, Patent Document 1). However, this method is intended to reproduce video and sound contents while synchronizing sound and a video, so that a user can visually recognize the audio-visual contents. Hence, it is difficult to apply the method to short-time video display for preventing a doctor from overlooking the lesion. Non-Patent Document 1: "M2A(R) Capsule Endoscopy Given(R) Diagnostic System", [online], Given Imaging Ltd., [searched on Mar. 9, 2005], the Internet URL is: http://www.givenimaging.com/NR/rdonlyres/76C20644-4B5B-496 4-811A-071E8133F83A/0/GI Marketing Brochure 2003.pdf. Non-Patent Document 2: B. Shahraray, "Scene change detection and content-based sampling of video sequences," Proc. IS&T/SPIE 2419, pp. 2-13, 1995 Non-Patent Document 3: D. Swanberg, C.-F. Shu, R. Jain, "Knowledge guided parsing in video databases," Proc. SPIE Conf. 1908, 1993, pp. 13-24.

Patent Document 1: Japanese Laid-Open Patent Application No. 10-243351

DISCLOSURE OF INVENTION

Problems that Invention is to Solve

The present invention has been conceived to solve the above-described problem, and an object of the present invention is to provide a capsule endoscope image display controller and the like that prevent a doctor from overlooking the lesion, without placing an excessive burden on him/her.

Means to Solve the Problems

In order to achieve the above object, a capsule endoscope image display controller controls display of an image sequence including plural images captured by a capsule endoscope which moves within digestive organs. The controller includes: an image-to-image similarity calculating unit which calculates, for each image included in the image sequence, a similarity between the image and a temporally consecutive image; an amount-of-movement calculating unit which calculates, for each image included in the image sequence, the amount of movement of a feature area included in the image; a video state classifying unit which classifies, for each image included in the image sequence, a video state of the image into one of the following states, based on the similarity and the amount of movement of the image: (a) "stationary state" indicating that the capsule endoscope is stationary; (b) "digestive organs deformation state" indicating that the digestive organs are deformed; and (c) "capsule moving state" indicating that the capsule endoscope is moving; a rendering duration determining unit which determines, for each image included in the image sequence, a rendering duration between the image and the temporally consecutive image, based on the video state, the similarity, and the amount of movement of the image; and a display controlling unit which sequentially displays, on a screen, the images included in the image sequence with the determined rendering durations.

As such, the capsule endoscope image display controller determines a rendering duration based on a video state of an image, a similarity between images, and the amount of movement. Thus, for example, in the case where the similarity is great and the amount of movement is large, it is considered that there is a moving partial area within the digestive organs, and thus there is a need not to overlook the possible presence of the lesion there. In such a case, by increasing the rendering duration, it becomes possible to display an image sequence so that an examining doctor does not overlook the lesion. When both the similarity and the amount of movement are small, the change between images is small, and thus by reducing the rendering duration, an image sequence can be played back at high speed. Accordingly, the examining doctor can carry out an endoscopic examination in a short period of time without overlooking the lesion.

In addition, by classifying in advance a video state, a rendering duration according to the video state can be appropriately determined. For example, when the video state is classified into a "stationary state", the rendering duration is shortened so that an image sequence can be displayed at high speed.

In addition, the capsule endoscope image display controller may further include a focused-feature-value extracting unit which extracts a predetermined feature value from each image included in the image sequence. The rendering duration determining unit may determine, for each image included in the image sequence, a rendering duration between the image and the temporally consecutive image, based on the similarity, the amount of movement, and the predetermined feature value of the image. For example, the predetermined feature value is a proportion of a red area in the whole area of the image.

When, for example, bleeding is occurring within the digestive organs, it is highly possible that there is a lesion. Hence, in such a case, by extending the rendering duration, it is possible to display an image sequence so that the examining doctor does not overlook the lesion.

In addition, the rendering duration determining unit may further determine the rendering duration based on the skill level of a user who monitors the image sequence to be displayed on the screen and carries out an endoscopic examination.

By determining a rendering duration taking into consideration a skill level of an examining doctor, in the case of a skilled examining doctor, an endoscopic examination can be carried out in a short period of time.

In addition, the rendering duration determining unit may further smooth the plural rendering durations of the obtained image sequence.

By smoothing a plurality of rendering durations arranged in time series, the use of a smoothing filter such as a Gaussian filter can slow down the change in rendering duration. Hence, even in the case where a stationary area in an image has suddenly moved, it is possible to allow the examining doctor's eyes to follow the change in image.

The present invention can be implemented not only as a capsule endoscope image display controller including such characteristic units but also as an image processing method that includes steps corresponding to the characteristic units included in the capsule endoscope image display controller, or as a program that causes a computer to execute the characteristic steps included in the image processing method. Needless to say, such a program can be distributed through storage media, such as CD-ROMs (Compact Disc-Read Only Memory), or communication networks, such as the Internet.

Effects of the Invention

With the present invention, it is possible to provide a capsule endoscope image display controller and the like that prevent a doctor from overlooking the lesion, without placing an excessive burden on him/her.

BRIEF DESCRIPTION OF DRAWINGS

FIG. 7 is a detailed flowchart of a video state classification process (54 in FIG. 4).

NUMERICAL REFERENCES

Figure 1:
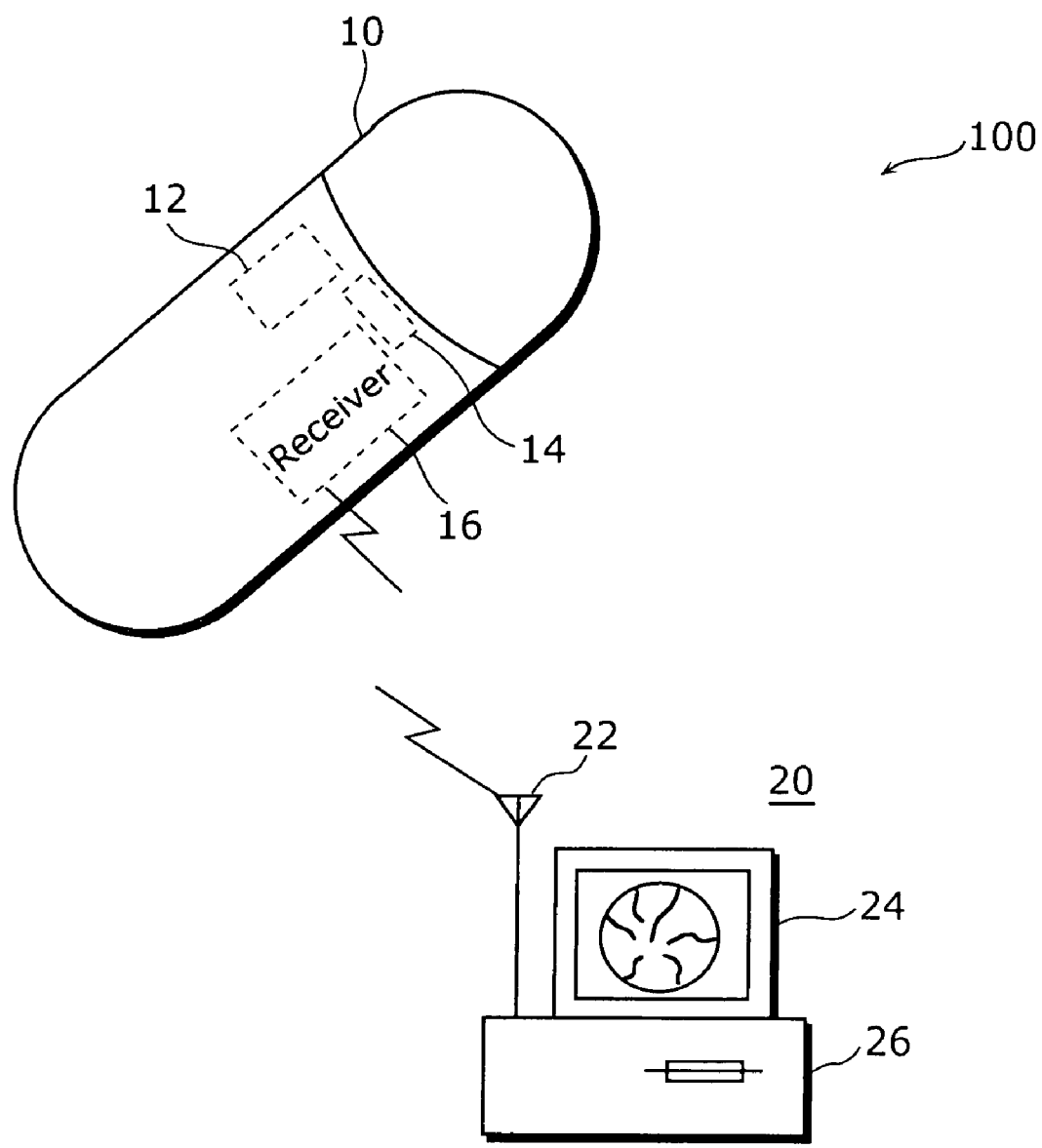
FIG. 1 is an external view showing a structure of an endoscope system.

10 Capsule endoscope
12 Lighting
14 Imaging unit
16 Receiver
20 Video display system
22 Antenna
24 Display
26 Capsule endoscope image display controller
32 Image receiving unit
34 Image accumulating unit
35 Whole image similarity calculating unit
36 Image similarity calculating unit
37 Partial image similarity calculating unit
38 Maximum-amount-of-movement calculating unit
39 Edge calculating unit
40 Focused-feature-value calculating unit
41 Video state classifying unit
42 Rendering duration determining unit
43 Feature area extracting unit
44 Display controlling unit
45 Amount-of-movement-of-feature-area calculating unit
47 Amount-of-movement calculating unit
100 Endoscope system

BEST MODE FOR CARRYING OUT THE INVENTION

An endoscope system according to an embodiment of the present invention will be described below with reference to the drawings.

FIG. 1 is an external view showing a structure of an endoscope system.

An endoscope system 100 includes: a capsule endoscope 10, and a video display system 20 that displays a video imaged by the capsule endoscope 10.

The capsule endoscope 10 is an apparatus for imaging a video of the inside of the digestive organs and includes an imaging unit 14 that images an object in front thereof and at the sides thereof, a lighting 12, and a receiver 16. A video (image sequence) imaged by the imaging unit 14 is distributed to the video display system 20 provided outside and the video display system 20 performs image processing and video display. For example, for the capsule endoscope 10, a capsule endoscope described in the aforementioned Non-Patent Document 1 or the like is used. In the capsule endoscope 10, a CMOS with low power consumption or the like is used for the imaging unit 14 and the imaging unit 14 captures images of two frames in one second. Hence, during a time period of about eight hours, about sixty thousand images in total can be captured.

The video display system 20 includes an antenna 22, a capsule endoscope image display controller 26, and a display 24. The antenna 22 receives a video distributed from the capsule endoscope 10. The capsule endoscope image display controller 26 is an apparatus that determines, based on the video received by the antenna 22, a rendering duration of the video and displays the video on the display 24 with the determined rendering duration.

Figure 2:
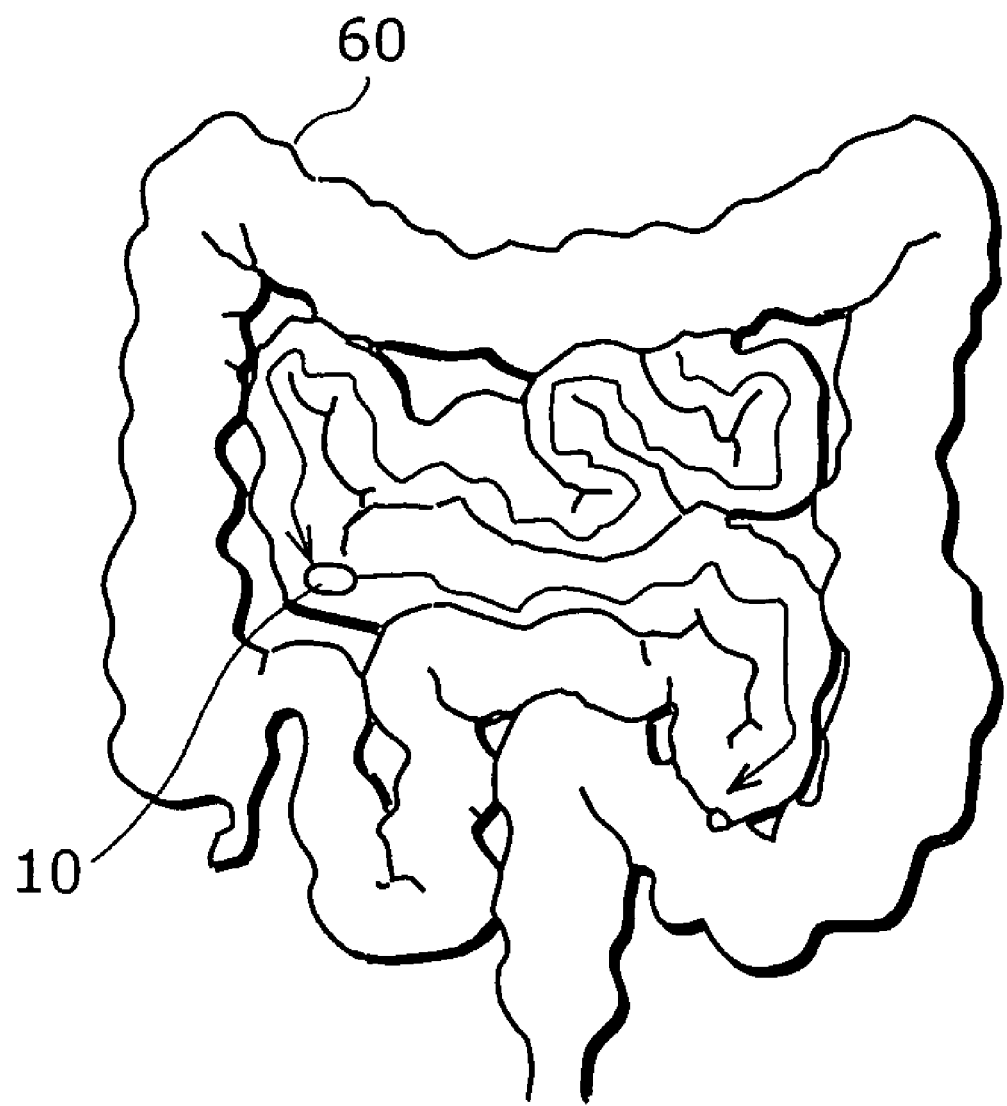
FIG. 2 is a diagram showing a scene in which a capsule endoscope moves in the small intestine.

FIG. 2 is a diagram showing a scene in which the capsule endoscope 10 moves in the small intestine. As shown by arrows in the drawing, the capsule endoscope 10 is advanced in a small intestine 60 from the mouth side to the anus side, according to the segmentation and peristaltic movements of the small intestine 60. Segmentation movement is a movement that occurs as a result of intermittent and simultaneous contractions of adjacent circular muscles inside the small intestine 60. Peristaltic movement is a movement that occurs by a combination of circular muscle and longitudinal muscle and is for pushing food forward.

Figure 3:
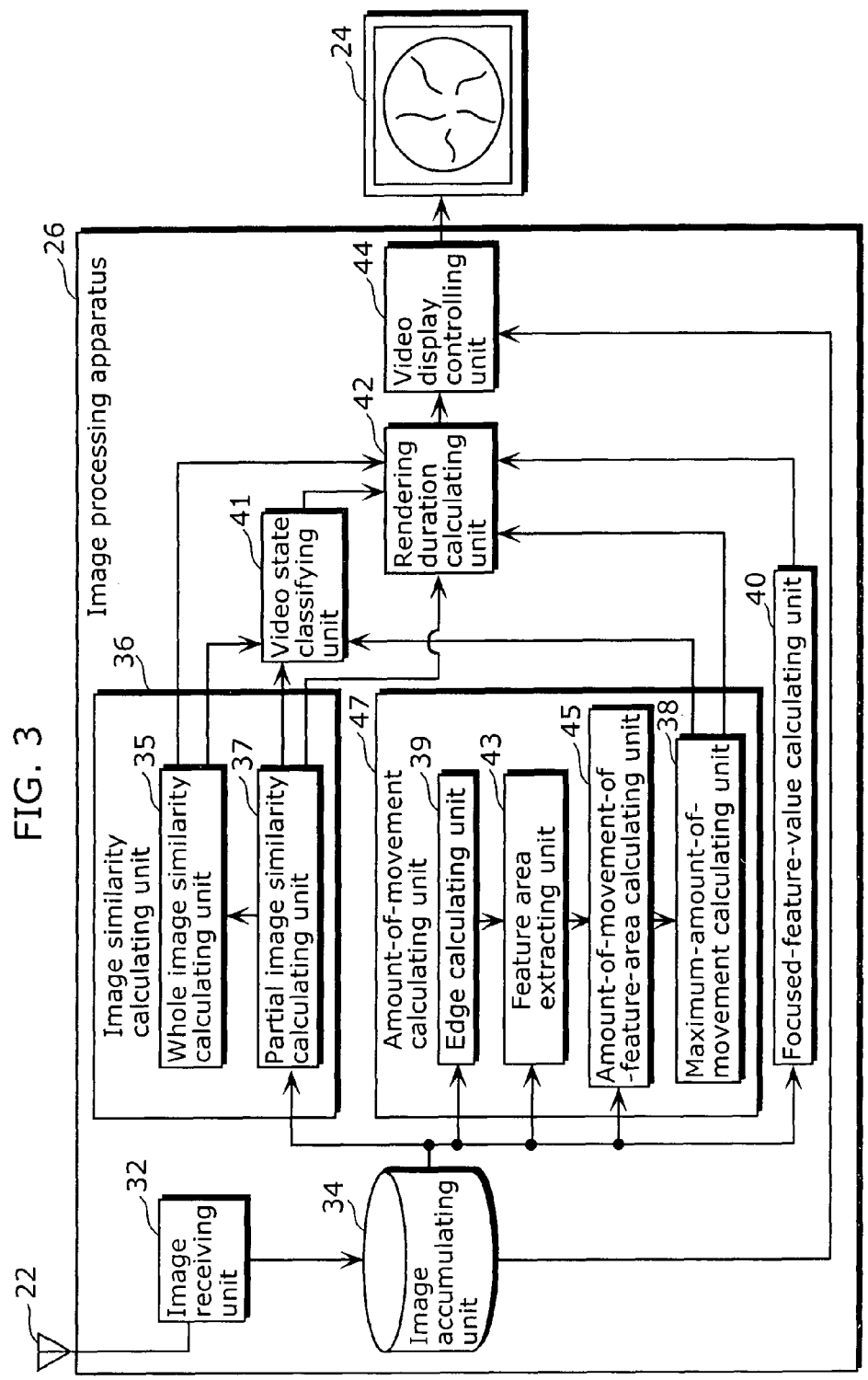
FIG. 3 is a block diagram showing a structure of a capsule endoscope image display controller.

FIG. 3 is a block diagram showing a structure of the capsule endoscope image display controller 26.

The capsule endoscope image display controller 26 includes an image receiving unit 32, an image accumulating unit 34, an image similarity calculating unit 36, an amount-of-movement calculating unit 47, a focused-feature-value calculating unit 40, a video state classifying unit 41, a rendering duration determining unit 42, and a display controlling unit 44.

The image receiving unit 32 is a processing unit that accumulates an image sequence to be transmitted from the capsule endoscope 10 which has received the image sequence via the antenna 22. The image accumulating unit 34 is a storage device that accumulates the image sequence imaged by the capsule endoscope 10.

The image similarity calculating unit 36 is an example of an image-to-image similarity calculating unit that calculates, for each image included in the image sequence, a similarity between the image and its temporally consecutive image, and includes a whole image similarity calculating unit 35 and a partial image similarity calculating unit 37.

The partial image similarity calculating unit 37 is a processing unit that calculates a partial image similarity which indicates to what degree parts of the respective temporally consecutive images are similar to each other. Specifically, as will be described later, the partial image similarity calculating unit 37 calculates, for each image included in the image sequence, a partial image similarity between blocks; that is, each of blocks divided from the image and its corresponding block in its temporally consecutive image.

The whole image similarity calculating unit 35 is a processing unit that calculates, for each image included in the image sequence, a whole image similarity between whole image areas; that is, the whole image areas of the image and its temporally consecutive image. Based on the partial image similarity calculated by the partial image similarity calculating unit 37, the whole image similarity calculating unit 35 calculates a whole image similarity which indicates to what degree the whole temporally consecutive images are similar to each other.

The amount-of-movement calculating unit 47 is an example of an amount-of-movement calculating unit that calculates, for each image included in the image sequence, the amount of movement of a feature area included in the image, and includes an edge calculating unit 39, a feature area extracting unit 43, an amount-of-movement-of-feature-area calculating unit 45, and a maximum-amount-of-movement calculating unit 38.

The edge calculating unit 39 is a processing unit that calculates, for each image included in the image sequence, the direction component of each edge included in the image and the edge strength.

The feature area extracting unit 43 is a processing unit that extracts a feature area from each image, based on the edge direction component and the edge strength.

The amount-of-movement-of-feature-area calculating unit 45 is a processing unit that extracts an area corresponding to the feature area from each image and its temporally consecutive image and calculates an amount of movement of the feature area.

The maximum-amount-of-movement calculating unit 38 is a processing unit that calculates a maximum amount of movement between temporally consecutive images which is a maximum value among amounts of movement of an area having a feature (hereinafter, referred to as the "maximum amount of movement"); that is, a maximum value among the amounts of movement of the feature area calculated by the amount-of-movement-of-feature-area calculating unit 45.

The focused-feature-value calculating unit 40 is an example of a focused-feature-value extracting unit that extracts a predetermined feature value from each image included in the image sequence, and is a processing unit that captures a feature (for example, the lesion or bleeding) or the like which draws the doctor's attention, as a feature value (hereinafter, referred to as the "focused feature value"), and calculates a value thereof.

The video state classifying unit 41 is an example of a video state classifying unit that classifies, based on the similarity and amount of movement of the image, the video state of each image included in the image sequence into one of the following states: (a) "stationary state" indicating that the capsule endoscope is stationary, (b) "digestive organ deformation state" indicating that the digestive organs are deformed, and (c) "capsule moving state" indicating that the capsule endoscope is moving. Specifically, the video state classifying unit 41 is a processing unit that classifies the attention image into one of the video states, based on a whole image similarity, a partial image similarity, and a maximum amount of movement.

The rendering duration determining unit 42 is an example of a rendering duration determining unit that determines, for each image included in the image sequence, a rendering duration between the image and its temporally consecutive image, based on the video state, similarity, and amount of movement of the image. Specifically, the rendering duration determining unit 42 is a processing unit that determines a rendering duration of the attention image, based on the video state, whole image similarity, maximum amount of movement, and focused feature value of the image.

The display controlling unit 44 is an example of a display controlling unit that sequentially displays, on a screen, the respective images included in the image sequence with the determined rendering durations, and is a processing unit that performs control to display image sequences accumulated in the image accumulating unit 34 on the display 24, based on the determined rendering durations.

The capsule endoscope image display controller 26 is implemented by a personal computer or the like, each of the processing units that composes the capsule endoscope image display controller 26 is implemented as a program which is executed by a CPU (Central Processing Unit), and the image accumulating unit 34 is implemented by a storage apparatus such as a hard disk.

Figure 4:
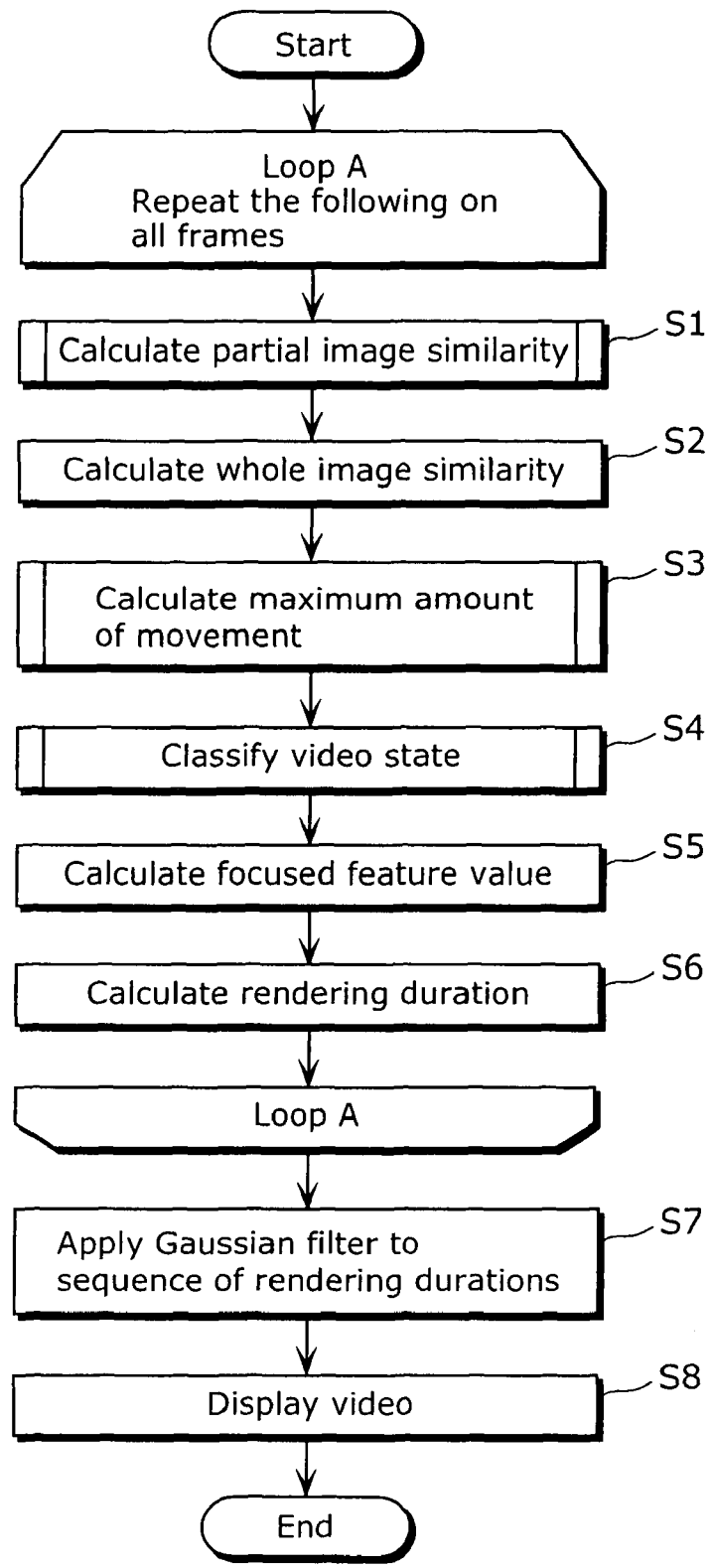
FIG. 4 is a flowchart showing a video display process performed by a video display system.

FIG. 4 is a flowchart showing a video display processing performed by the video display system 20. Here, it is assumed that N (N is a natural number) images of the inside of the small intestine which are imaged by the capsule endoscope 10 for about eight hours have already been accumulated in the image accumulating unit 34.

Each unit of the capsule endoscope image display controller 26 performs the following processing on each of N-frame images (Loop A). First, the partial image similarity calculating unit 37 calculates a partial image similarity of an n-th frame image to which attention is paid (S1). The partial image similarity in this embodiment indicates a similarity between each of 64 blocks in the n-th frame image and its corresponding block in an (n+1)-th frame image. The 64 blocks are obtained by dividing an image into eight blocks vertically and horizontally. Namely, when the block number is i, 64 values are obtained as partial image similarities sim(i) (i=1 to 64). The value of the partial image similarity sim(i) becomes closer to 1 as a similarity between two blocks becomes higher.

Figure 5:
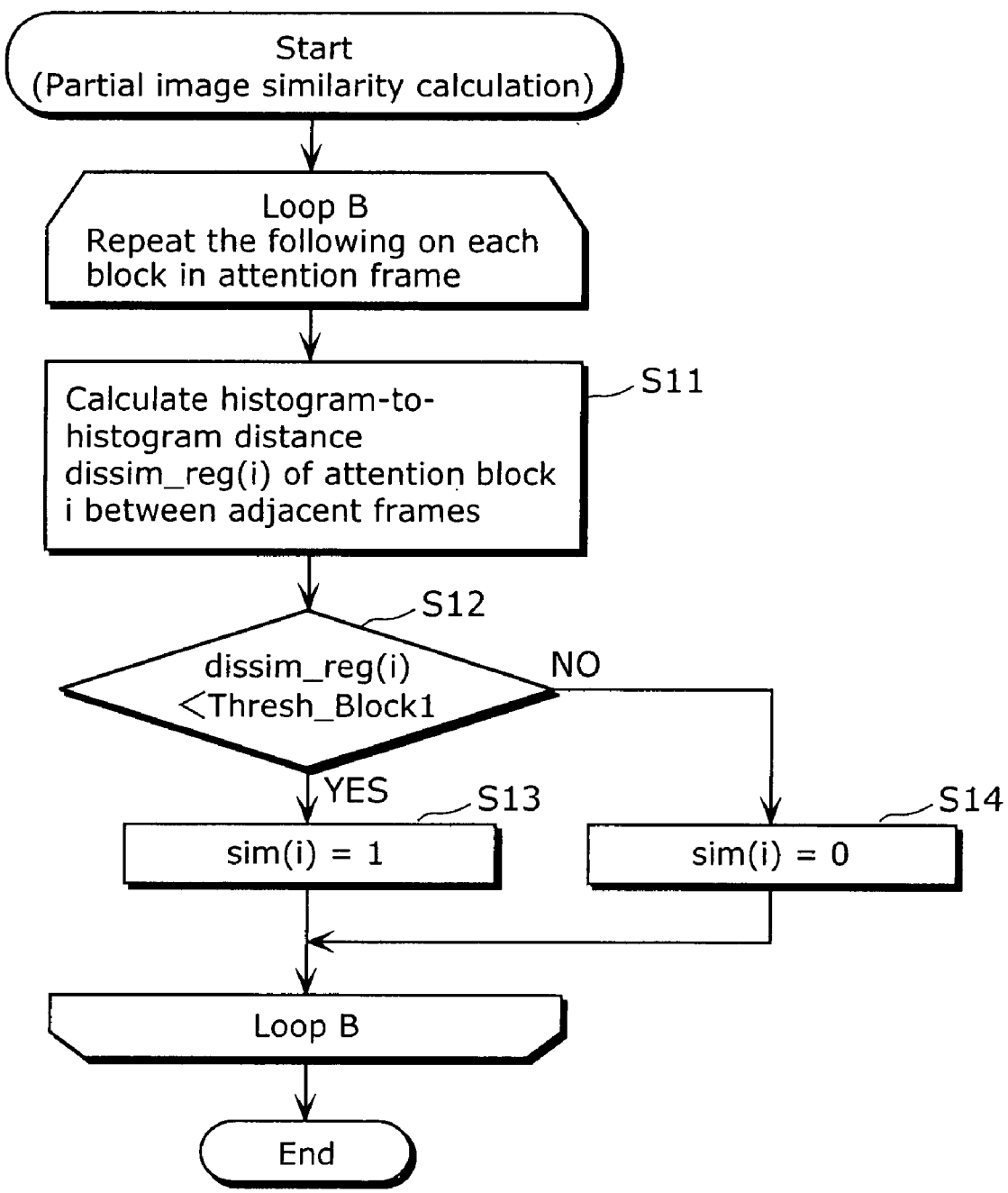
FIG. 5 is a detailed flowchart of a partial image similarity calculation process (S1 in FIG. 4).

FIG. 5 is a detailed flowchart of the partial image similarity calculation processing (S1). At the partial image similarity calculation processing (S1), the similarity is calculated using color information on an image. One frame image includes three images, R (Red), G (Green), and B (Blue) images. For color evaluation, plural color spaces (YIQ, HSV, L*a*b*, etc.) are known, but here for simplicity of processing, an RGB space is used.

The partial image similarity calculating unit 37 repeats the following processing on each of 64 blocks included in the n-th frame image to which attention is paid (Loop B). Specifically, the partial image similarity calculating unit 37 calculates a histogram-to-histogram distance dissim_reg(i) of an i-th block to which attention is paid, based on the following Expression (1) (S11).

[Equation 1] (1)

$$\mathrm{dissim\_reg}(i) = \sum_{k=1}^{16} (|H_{R,k}^{(n)} - H_{R,k}^{(n+1)}| + |H_{G,k}^{(n)} - H_{G,k}^{(n+1)}| + |H_{B,k}^{(n)} - H_{B,k}^{(n+1)}|)$$

The pixel values in each of RGB color planes in each block are classified into 16 levels in a histogram of each block. For example, $H_{R,k}^{(n)}$ represents a value of a k-th level in an R plane histogram of an i-th block in an n frame. Here, a histogram has 16 levels; thus, for example, when the pixel values have 256 gradation levels, each level in the histogram corresponds to 16 (=256/16) gradation levels of the pixel values.

The partial image similarity calculating unit 37 determines whether the histogram-to-histogram distance dissim_reg(i) of the i-th block is less than a predetermined threshold value Thresh_Block1 (S12). If, as a result of the determination, the histogram-to-histogram distance dissim_reg(i) is less than the threshold value Thresh_Block1 (YES in S12), then 1 is assigned to a partial image similarity sim(i) (S13). If the histogram-to-histogram distance dissim_reg(i) is greater than or equal to the threshold value Thresh_Block1 (NO in S12), then 0 is assigned to the partial image similarity sim(i) (S14).

The partial image similarity calculating unit 37 performs the above processing on all of 64 blocks included in the n-th frame image to which attention is paid, in the manner described above (Loop B).

Referring back to FIG. 4, the whole image similarity calculating unit 35 calculates a whole image similarity Similarity(n) between the n-th frame image and the (n+1)-th frame image, based on the 64 partial image similarities sim(i) (i=1 to 64) obtained in the partial image similarity calculation processing (S1 in FIG. 4 and FIG. 5) (S2). The whole image similarity calculating unit 35 calculates the whole image similarity Similarity(n) between the n-th frame image and the n+1-th frame image according to the following Expression (2).

[Equation 2] (2)

$$\mathrm{Similarity}(n) = \sum_{i=1}^{64} sim(i)/64$$

Specifically, the whole image similarity Similarity(n) takes a numerical value between 0 and 1, and indicates that the closer the value is to 1 the higher the similarity is between the n-th frame image and the (n+1)-th frame image and indicates that the closer the value is to 0 the lower the similarity is between them.

Then, the amount-of-movement calculating unit 47 calculates a maximum amount of movement motion(n) in the n-th frame (S3). A calculation method for the maximum amount of movement motion(n) will be described in detail later. The maximum amount of movement motion(n) takes a value between 0 and 1 and indicates that the closer the value is to 1 the greater the movement of a feature area is in the image.

Figure 6:
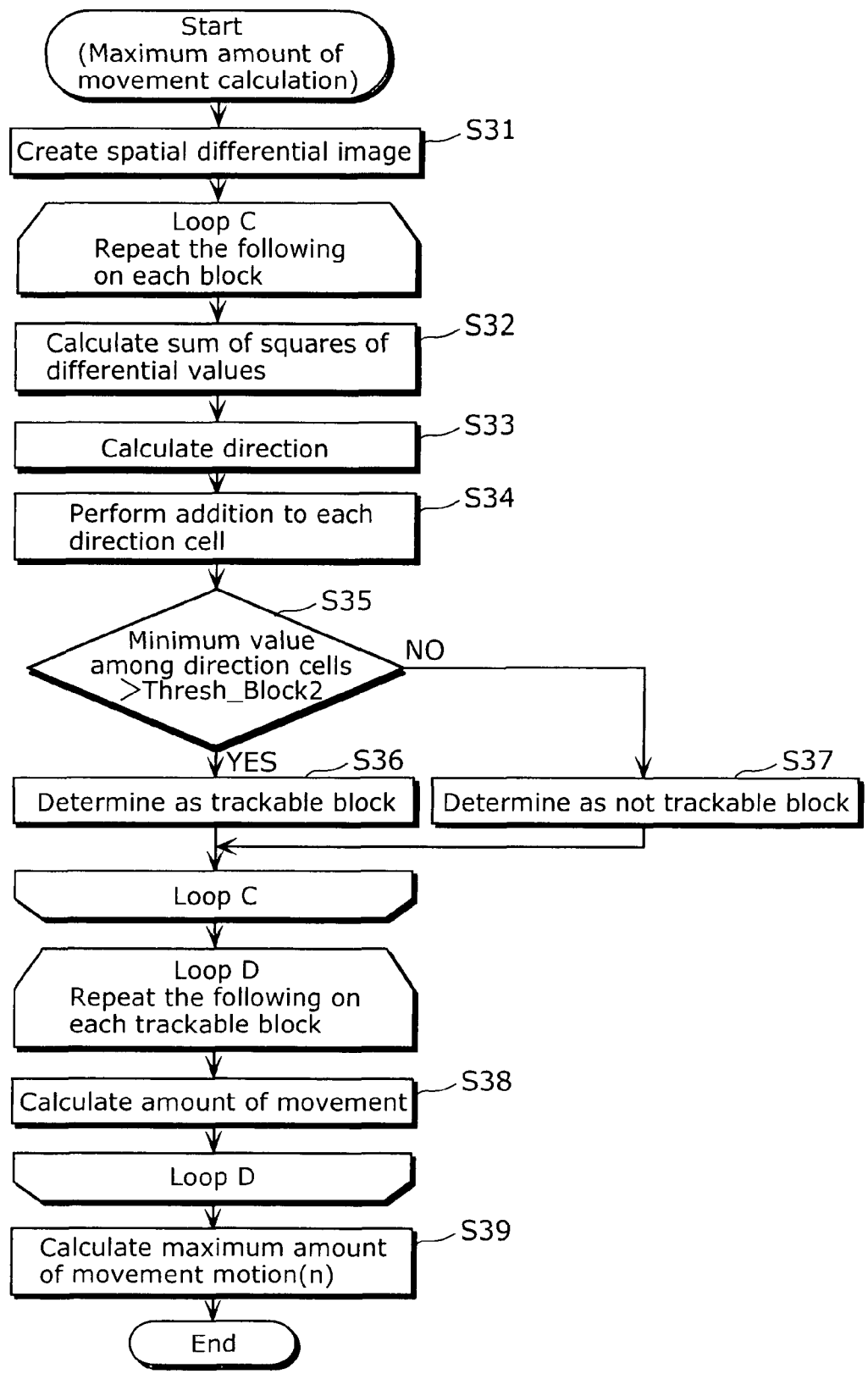
FIG. 6 is a detailed flowchart of a maximum-amount-of-movement calculation process (S3 in FIG. 4).

FIG. 6 is a detailed flowchart of the maximum-amount-of-movement calculation processing (S3 in FIG. 4).

The edge calculating unit 39 employs an x-direction differential filter and a y-direction differential filter for an n-th frame image I to which attention is paid and thereby obtains an x-direction differential value $I_x(x,y)$ and a y-direction differential value $I_y(x,y)$ and then creates an x-direction spatial differential image $I_x$ and a y-direction spatial differential image $I_y$ (S31). As a differential filter, a generic special differential filter such as a Sobel filter or a Roberts filter can be used.

Subsequently, the feature area extracting unit 43 repeats the following processing on each block included in the n-th frame image I (Loop C). Note that it is assumed that the size of a block is 16×16 pixels, for example; however, this is merely an example and thus any size other than the above may be used.

First, the feature area extracting unit 43 obtains a sum of squares $S(x,y)^2$ of differential values of pixels (x,y) in the n-th frame image I to which attention is paid, according to the following Expression (3) (S32).

$$S(x,y)^2 = I_x(x,y)^2 + I_y(x,y)^2 \quad (3)$$

In addition, the feature area extracting unit 43 calculates a direction α(x,y) of each pixel (x,y) based on the differential values $I_x(x,y)$ and $I_y(x,y)$, according to the following Expression (4) (S33).

[Equation 3]

$$\alpha(x, y) = \tan^{-1} \frac{I_y(x, y)}{I_x(x, y)} \qquad (4)$$

Then, the feature area extracting unit 43 adds a value shown by the following Expression (5), to six direction cells C(i) (i=0 to 5) (S34).

[Equation 4]

$$S(x,y)^2 \cos^2(\alpha(x,y) - i*\pi/6) \qquad (5)$$

Here, each direction cell C(i) (i=0 to 5) corresponds to one obtained by dividing angles from 0 (rad) (0°) to π (rad) (180°) by six. For example, a value obtained by adding the value to C(0) represents the strength of a direction component (the reliability of a direction component) present between 0° and 30°.

Next, the feature area extracting unit 43 checks whether a minimum value among the six direction cells is greater than a predetermined threshold value Thresh_Block2 (S35). That the minimum value among the direction cells is greater than the predetermined threshold value Thresh_Block2 indicates that a block has therein edge components in plural directions and has a characteristic pattern such as a texture. Thus, when the above-described condition is satisfied (YES in S35), the feature area extracting unit 43 determines that the block is a trackable block (S36). On the other hand, when the above-described condition is not satisfied, it is determined that a pattern in the block is not a characteristic pattern and thus the feature area extracting unit 43 does not determine that the block is a trackable block (S37).

Subsequently, the amount-of-movement-of-feature-area calculating unit 45 repeats an amount of movement calculation processing (S38), as will be described later, on each block that is determined to be a trackable block. The amount-of-movement-of-feature-area calculating unit 45 searches, the (n+1)-th frame image, for a location corresponding to a trackable block obtained from the n-th frame image (S38). Specifically, the amount-of-movement-of-feature-area calculating unit 45 obtains a value of the following Expression (6) in a search area near the location (x,y) of a trackable block in an n-th frame image $I^{(n)}$ and obtains the location (x+a,y+b) where the value is smallest.

[Equation 5]

$$\sum_{a,b} (I^{(n)}(x, y) - I^{(n+1)}(x + a, y + b))^2 \qquad (6)$$

Here, $I^{(n)}(x,y)$ represents a pixel value at coordinates (x,y) in the n-th frame image.

Thus, an amount of movement of an i-th trackable block BlockMotion(i) can be obtained based on the location (x+a, y+b) where the value of Expression (6) is smallest, according to the following Expression (7).

[Equation 6]

$$BlockMotion(i) = \sqrt{a^2 + b^2} \qquad (7)$$

Then, the maximum-amount-of-movement calculating unit 38 normalizes a maximum value among all of the obtained amounts of movement of trackable blocks, according to the following Expression (8) and calculates a maximum amount of movement of the n-th frame image motion(n) (S39).

[Equation 7]

$$motion(n) = \max_i \{BlockMotion(i)\} / MaxSearch \qquad (8)$$

Here, MaxSearch is a maximum amount of movement that can be taken when a trackable block is searched within a search area.

Referring back to FIG. 4, the video state classifying unit 41 checks what state the n-th frame image is in, based on the histogram-to-histogram distance dissim_reg(i), the whole image similarity Similarity(n), and the maximum amount of movement motion(n) in the n-th frame, and performs a video state classification (S4). A video state classification processing will be described later. The video state classifying unit 41 classifies the n-th frame image into one of the following states: a "stationary state" indicating that the capsule endoscope 10 is stationary, a "minute area deformation state" indicating that a minute area is deformed in the image, a "small intestine deformation state" indicating that the small intestine is deformed, and a "capsule moving state" indicating that the capsule endoscope 10 is moving.

FIG. 7 is a detailed flowchart of the video state classification processing (S4 in FIG. 4).

The video state classifying unit 41 determines whether the whole image similarity Similarity(n) in the n-th frame is greater than a threshold value Thresh1 (S41). If the whole image similarity Similarity(n) is greater than the threshold value Thresh1 (YES in S41), then the video state classifying unit 41 checks whether a maximum value max{dissim_reg (i)} among the histogram-to-histogram distances dissim_reg (i) obtained by the partial image similarity calculating unit 37 is less than or equal to a threshold value Thresh2 (S42).

When both conditions in S41 and S42 are satisfied (YES in S41 and YES in S42), it indicates that the image has similarity even when viewed consecutive frames as a whole and there are no similar blocks even when viewed block by block. Hence, in such a case, the video state classifying unit 41 forcefully sets 0 to the maximum amount of movement motion(n) (S43) and classifies the frame into a "stationary state".

If the maximum value max{dissim_reg(i)} among the histogram-to-histogram distances dissim_reg(i) is greater than the threshold value Thresh2 (NO in S42), then the video state classifying unit 41 checks whether the maximum amount of movement motion(n) is less than or equal to a threshold value Thresh3 (S45). When the condition in S45 is satisfied (YES in S45), although there is a difference between frames when viewed block by block (NO in S42), the maximum amount of movement motion(n) is small (YES in S45) and thus the video state classifying unit 41 classifies the frame into a "stationary state" (S44).

When the condition in S45 is not satisfied (NO in S45), although consecutive frame images are similar when viewed as a whole images (YES in S41), there is a difference between the frames when viewed block by block (NO in S42) and the maximum amount of movement motion(n) has a large value. Thus the video state classifying unit 41 determines that a minute area, such as the lesion, has moved significantly between the images and accordingly classifies the frame into a "minute area deformation state" (S46).

If the whole image similarity Similarity(n) in the n-th frame is less than or equal to the threshold value Thresh1 (NO in S41), then the video state classifying unit 41 determines whether a minimum value min{dissim_reg(i)} among the histogram-to-histogram distances dissim_reg(i) is greater than or equal to a predetermined threshold value Thresh4 (S47).

When the condition in S47 is satisfied (YES in S47), it indicates that whole images in consecutive frames are dissimilar (NO in S41) and every block in the image has a great amount of movement (YES in S47). Thus, the video state classifying unit 41 forcefully sets 1 to the maximum amount of movement motion(n) (S50) and classifies the frame into a "capsule moving state" (S51).

When the condition at S47 is not satisfied (NO in S47), the video state classifying unit 41 checks whether the maximum amount of movement motion(n) is greater than or equal to a threshold value Thresh5 (S48). When the condition at S48 is satisfied (YES in S48), the video state classifying unit 41 classifies the frame into a "capsule moving state" (S51).

When the condition at S48 is not satisfied (NO in S48), the video state classifying unit 41 classifies the frame into a "small intestine deformation state" (S49).

When, in the above video state classification process, the condition in S41 is satisfied (YES in S41, S42 to S46), the overall change between images is small. Thus, a maximum amount of movement motion(n) obtained between the images has high reliability. On the other hand, when the condition in S41 is not satisfied (NO in S41, 547 to S51), the overall change between images is remarkable. Thus, a maximum amount of movement motion(n) obtained between the images has low reliability. Hence, the "minute area deformation state" can also be considered to be deformation of the small intestine in the case where the reliability of a maximum amount of movement motion(n) is high, and the "small intestine deformation state" can also be considered to be deformation of the small intestine in the case where the reliability of a maximum amount of movement motion(n) is low. Accordingly, in the Claims, the "minute area deformation state" and "small intestine deformation state" are collectively represented as a "digestive organs deformation state".

Even when, in the aforementioned video state classification process, an image is classified into a "stationary state", the capsule endoscope 10 is not always stationary. Namely, also in the case where the capsule endoscope 10 is moving but seems to be stationary, a frame is classified into a stationary state.

Referring back to FIG. 4, the focused-feature-value calculating unit 40 calculates a focused feature value $Abn^{(n)}$ in the n-th frame image (S5). In this embodiment, the occurrence of bleeding in the small intestine is captured, and thus, when an area having red color components has an area of predetermined threshold value or above, $Abn^{(n)}$ is determined as 1, and otherwise $Abn^{(n)}$ is determined as 0. The determination as to whether there is a red color component is made as follows. For example, when the pixel value in the R plane is greater than or equal to a predetermined threshold value and the pixel values in the G and B planes are less than or equal to a predetermined threshold value, it is determined that there is a red component. Note that any other determination method may be used. The focused feature value does not need to be the aforementioned feature value indicating whether a bleeding state is present and may be a feature value indicating whether the lesion is present.

Then, the rendering duration determining unit 42 obtains, according to the classification result of a video state, a rendering duration TimeDuration(n) between the n-th frame image and the (n+1)-th frame image (S6). By changing the rendering duration, the video playback speed can be changed. The rendering duration depends on the system and has a predetermined upper limit. When the video state is in a "stationary state", a rendering speed that is the system's highest performance is set, and thus the rendering duration determining unit 42 calculates the rendering duration TimeDuration(n) using a system-dependent constant const(System), based on the following Expression (9).

When the video state is in a "capsule moving state", the rendering duration needs to be set to the longest duration and it depends on the skill level skill(human) of the examining doctor. Hence, the rendering duration determining unit 42 calculates the rendering duration TimeDuration(n) using the following Expression (10).

When the video state is in a "minute area deformation state" or "small intestine deformation state", a similarity between images or blocks or the amount of movement between blocks is moderately present. Thus, by synthesizing them, a rendering duration is determined. In this case too, a change is made based on the skill level skill(human) of the examining doctor and the rendering duration determining unit 42 calculates the rendering duration TimeDuration(n) using the following Expression (11).

[Equation 8]

$$\text{TimeDuration}(n) = A_1 * \{1 - \text{Similarity}(n)\} + A_2 * \text{motion}(n) + \text{const(System)} \quad (9)$$

$$\text{TimeDuration}(n) = D_1 * \{1 - \text{Similarity}(n)\} + D_2 * \text{motion}(n) + +\text{skill(human)} + \text{const(System)} \quad (10)$$

$$\text{TimeDuration}(n) = [B * \{1 - \text{Similarity}(n)\} + (1-B) * \text{motion}(n)] * \text{skill(human)} + \text{const(System)} \quad (11)$$

On the other hand, when there is a possibility that the lesion may have been shot in an image to be observed by the examining doctor, careful observation is required. Hence, the rendering duration for such a time needs to be extended. Hence, the rendering duration of the image for such a time needs to be extended. Thus, by using the aforementioned focused feature value $Abn^{(n)}$, a final rendering duration is determined according to the following Expression (12).

$$\text{TimeDuration}(n) = \text{TimeDuration}(n) + \beta Abn^{(n)} \quad (12),$$

where $\beta$ is a predetermined constant.

According to the aforementioned method, in the case where the examining doctor needs to significantly move his/her line of sight on a screen, the rendering duration determining unit 42 makes a determination so that the rendering duration is extended. Note that "the case where the examining doctor needs to significantly move his/her line of sight on a screen" indicates the case where there is a large number of feature areas (hereinafter, referred to as "attention areas"), such as the lesion, to which the examining doctor needs to pay attention or the case where the amount of movement in an attention area is great. The number of attention areas can be obtained based on a histogram-to-histogram distance and the amount of movement in an attention area can be obtained based on a maximum amount of movement.

The above-described processing in S1 to S6 are performed on all frames and a rendering duration of each frame is calculated (the Loop A in FIG. 4). By, as in the above manner, classifying a video state based on a video feature value and changing a rendering duration, the video display speed can be changed. However, there may be a case where a sudden change in display speed may appear in video as a result of a video state transition. An example is a case where a stationary area is suddenly moved in an image. In such a case, there is a need to slow down the change in display speed so that the doctor's eyes can follow the change in the image. Hence, the rendering duration determining unit 42 employs a Gaussian filter for values of rendering durations arranged on the time axis, and thereby slowing down the change in rendering duration (S7). The Gaussian filter is known art, and thus a detailed description thereof is not repeated here.

The display controlling unit 44 controls to display, on the display 24, the image sequence accumulated in the image accumulating unit 34 so as to implement the rendering duration obtained ultimately (S8).

As described above, if a video shot by a capsule endoscope is played back at the same speed as the video is shot, an examination also requires about eight hours or more, constraining an examining doctor for a long time; thus, it is not realistic. At present, it takes about one hour for even a skilled examining doctor to perform an examination, and for a non-skilled person, it takes about three hours. The video includes, in about eight hours, both a time zone where a site moves quickly and a time zone where the site moves slowly or does not move, and thus there is a need not to miss a change of the site. By using the technique proposed by the present invention, rendering of a video can be automatically slowed down in a time zone where a site moves quickly and rendering can be automatically speeded up in a time zone where the site moves slowly or does not move. In addition, when the capsule endoscope moves in the small intestine, the examining doctor can observe the video at a constant speed. Hence, for example, even at 10× speed (about 50 minutes) on average, an examination can be performed. In addition, although even a skilled person takes, a 14× speed as the maximum speed in conventional methods, there is no risk of oversight even when 14× speed is taken as the average speed. Hence, it becomes possible to observe the whole video in about 35 minutes. By this, it becomes possible to carry out an endoscopic examination of the small intestine that is almost never carried out conventionally.

INDUSTRIAL APPLICABILITY

The present invention can be applied to an image processing apparatus, etc., with which a video can be viewed at high speed, and can be applied particularly to a capsule endoscope image display controller, etc., with which a video imaged by a capsule endoscope can be viewed at high speed.

The invention claimed is:

1. A capsule endoscope image display controller that controls display of an image sequence including a plurality of images captured by a capsule endoscope which moves within digestive organs, said controller comprising:
an image-to-image similarity calculating unit operable to calculate, for each image included in the image sequence, a similarity between the image and a temporally consecutive image;
an amount-of-movement calculating unit operable to calculate, for each image included in the image sequence, an amount of movement of a feature area included in the image;
a video state classifying unit operable to classify, for each image included in the image sequence, a video state of the image into one of a plurality of states including at least the following states, based on the similarity and the amount of movement of the image:
(a) "stationary state" indicating that the capsule endoscope is stationary;
(b) "digestive organs deformation state" indicating that the digestive organs are deformed; and
(c) "capsule moving state" indicating that the capsule endoscope is moving;
a rendering duration determining unit operable to determine, for each image included in the image sequence, a rendering duration between the image and the temporally consecutive image, based on the video state, the similarity, and the amount of movement of the image; and
a display controlling unit operable to sequentially display, on a screen, the images included in the image sequence with the determined rendering durations.

2. The capsule endoscope image display controller according to claim 1,
wherein said image-to-image similarity calculating unit includes:
a whole image similarity calculating unit operable to calculate, for each image included in the image sequence, a whole image similarity between the image and the temporally consecutive image, the whole image similarity being a similarity between a whole area of the image and a whole area of the temporally consecutive image areas; and
a partial image similarity calculating unit operable to calculate, for each image included in the image sequence, a partial image similarity between each of blocks divided from the image and a corresponding block in the temporally consecutive image, the partial image similarity being a similarity between the blocks,
wherein said rendering duration determining unit is operable to determine, for each image included in the image sequence, a rendering duration between the image and the temporally consecutive image, based on the video state, the whole image similarity, the partial image similarity, and the amount of movement of the image.

3. The capsule endoscope image display controller according to claim 2,
wherein said partial image similarity calculating unit is operable to calculate, for each image included in the image sequence, a histogram-to-histogram distance between each of the blocks divided from the image and the corresponding block in the temporally consecutive image, and calculate a partial image similarity based on the histogram-to-histogram distance, the histogram-to-histogram distance being a sum of absolute values of differences between pixel values and the partial image similarity being a similarity between the blocks, and
said video state classifying unit is operable to classify, for each image included in the image sequence, the image into the "stationary state" when the following condition (i) or condition (ii) is satisfied:
the condition (i) being that the whole image similarity of the image is greater than a first threshold value and a maximum value among a plurality of histogram-to-histogram distances of a plurality of blocks included in the image is less than or equal to a second threshold value; and
the condition (ii) being that the whole image similarity of the image is greater than the first threshold value, the maximum value among the plurality of histogram-to-histogram distances of the plurality of blocks included in the image is greater than the second threshold value, and a maximum amount of movement is less than or equal to a third threshold value, the maximum amount of movement being a maximum value among amounts of movement of the feature area included in the image.

4. The capsule endoscope image display controller according to claim 2,
wherein said partial image similarity calculating unit is operable to calculate, for each image included in the image sequence, a histogram-to-histogram distance between each of the blocks divided from the image and the corresponding block in the temporally consecutive image, and calculate a partial image similarity based on the histogram-to-histogram distance, the histogram-to-histogram distance being a sum of absolute values of differences between pixel values and the partial image similarity being a similarity between the blocks, and
said video state classifying unit is operable to classify, for each image included in the image sequence, the image into the "digestive organs deformation state" when the following condition (iii) or condition (iv) is satisfied:
the condition (iii) being that the whole image similarity of the image is greater than a first threshold value, a maximum value among a plurality of histogram-to-histogram distances of a plurality of blocks included in the image is greater than a second threshold value, and a maximum amount of movement is greater than a third threshold value, the maximum amount of movement being a maximum value among amounts of movement of the feature area included in the image; and
the condition (iv) being that the whole image similarity of the image is less than or equal to the first threshold value, a minimum value among the plurality of histogram-to-histogram distances of the plurality of blocks included in the image is less than a fourth threshold value, and the maximum amount of movement is less than a fifth threshold value, the maximum amount of movement being the maximum value among the amounts of movement of the feature area included in the image.

5. The capsule endoscope image display controller according to claim 2,
wherein said partial image similarity calculating unit is operable to calculate, for each image included in the image sequence, a histogram-to-histogram distance between each of the blocks divided from the image and the corresponding block in the temporally consecutive image, and calculate a partial image similarity based on the histogram-to-histogram distance, the histogram-to-histogram distance being a sum of absolute values of differences between pixel values and the partial image similarity being a similarity between the blocks, and
said video state classifying unit is operable to classify, for each image included in the image sequence, the image into the "capsule moving state" when the following condition (v) or condition (vi) is satisfied:
the condition (v) being that the whole image similarity of the image is less than or equal to a first threshold value and a minimum value among a plurality of histogram-to-histogram distances of a plurality of blocks included in the image is greater than or equal to a fourth threshold value; and
the condition (vi) being that the whole image similarity of the image is less than or equal to the first threshold value, the minimum value among the plurality of histogram-to-histogram distances of the plurality of blocks included in the image is less than the fourth threshold value, and a maximum amount of movement is greater than or equal to a fifth threshold value, the maximum amount of movement being a maximum value among amounts of movement of the feature area included in the image.

6. The capsule endoscope image display controller according to claim 1,
wherein said amount-of-movement calculating unit includes:
an edge calculating unit operable to calculate, for each image included in the image sequence, a direction component of an edge included in the image and an edge strength;
a feature area extracting unit operable to extract, from each image, a feature area based on the edge direction component and the edge strength;
an amount-of-movement-of-feature-area calculating unit operable to extract an area corresponding to the feature area from each image and the temporally consecutive image, and calculate an amount of movement of the feature area; and
a maximum-amount-of-movement calculating unit operable to calculate a maximum amount of movement which is a maximum value among amounts of movement of the feature area,
wherein said rendering duration determining unit is operable to determine, for each image included in the image sequence, a rendering duration between the image and the temporally consecutive image, based on the video state, the similarity, and the maximum amount of movement of the image.

7. The capsule endoscope image display controller according to claim 1, further comprising
a focused-feature-value extracting unit operable to extract a predetermined feature value from each image included in the image sequence,
wherein said rendering duration determining unit is operable to determine, for each image included in the image sequence, a rendering duration between the image and the temporally consecutive image, based on the video state, the similarity, the amount of movement, and the predetermined feature value of the image.

8. The capsule endoscope image display controller according to claim 7,
wherein the predetermined feature value is a proportion of a red area in a whole area of the image.

9. The capsule endoscope image display controller according to claim 1,
wherein said rendering duration determining unit is further operable to determine the rendering duration based on a skill level of a user who monitors the image sequence to be displayed on the screen and carries out an endoscopic examination.

10. The capsule endoscope image display controller according to claim 1,
wherein said rendering duration determining unit is further operable to smooth the plurality of rendering durations of the obtained image sequence.

11. A capsule endoscope image display control method for controlling display of an image sequence including a plurality of images captured by a capsule endoscope which moves within digestive organs, said method comprising:
a step of calculating, for each image included in the image sequence, a similarity between the image and a temporally consecutive image;
a step of calculating, for each image included in the image sequence, an amount of movement of a feature area included in the image;
a step of classifying, for each image included in the image sequence, a video state of the image into one of a plurality of states including at least the following states, based on the similarity and the amount of movement of the image:
(a) "stationary state" indicating that the capsule endoscope is stationary;
(b) "digestive organs deformation state" indicating that the digestive organs are deformed; and
(c) "capsule moving state" indicating that the capsule endoscope is moving;

a step of determining, for each image included in the image sequence, a rendering duration between the image and the temporally consecutive image, based on the video state, the similarity, and the amount of movement of the image; and a step of sequentially displaying, on a screen, the images included in the image sequence with the determined rendering durations.

12. A non-transitory computer-readable storage medium having stored therein a program that controls display of an image sequence including a plurality of images captured by a capsule endoscope which moves within digestive organs, said program causing a computer to perform:

a step of calculating, for each image included in the image sequence, a similarity between the image and a temporally consecutive image;

a step of calculating, for each image included in the image sequence, an amount of movement of a feature area included in the image;

a step of classifying, for each image included in the image sequence, a video state of the image into one of a plurality of states including at least the following states, based on the similarity and the amount of movement of the image:
(a) "stationary state" indicating that the capsule endoscope is stationary;
(b) "digestive organs deformation state" indicating that the digestive organs are deformed; and
(c) "capsule moving state" indicating that the capsule endoscope is moving;

a step of determining, for each image included in the image sequence, a rendering duration between the image and the temporally consecutive image, based on the video state, the similarity, and the amount of movement of the image; and a step of sequentially displaying, on a screen, the images included in the image sequence with the determined rendering durations.

* * * * *